United States Patent
Narayanan et al.

(10) Patent No.: US 8,787,643 B2
(45) Date of Patent: Jul. 22, 2014

(54) FUNCTIONAL IMAGING

(75) Inventors: Manoj V. Narayanan, Snohomish, WA (US); Jens-Christoph Georgi, Aachen (DE); Frank O. Thiele, Seattle, WA (US); Ralph Brinks, Hagen (DE); Michael Perkuhn, Bocholz (NL)

(73) Assignee: Koninklijke Philips B.V., Eindhoven (NL)

( * ) Notice: Subject to any disclaimer, the term of this patent is extended or adjusted under 35 U.S.C. 154(b) by 345 days.

(21) Appl. No.: 13/147,402

(22) PCT Filed: Jan. 12, 2010

(86) PCT No.: PCT/IB2010/050113
§ 371 (c)(1),
(2), (4) Date: Aug. 2, 2011

(87) PCT Pub. No.: WO2010/095065
PCT Pub. Date: Aug. 26, 2010

(65) Prior Publication Data
US 2011/0293143 A1 Dec. 1, 2011

Related U.S. Application Data

(60) Provisional application No. 61/152,986, filed on Feb. 17, 2009.

(51) Int. Cl.
*G06K 9/00* (2006.01)
*G06T 7/00* (2006.01)
*A61B 6/00* (2006.01)

(52) U.S. Cl.
CPC ..... *G06T 7/0028* (2013.01); *G06T 2207/10104* (2013.01); *G06T 2207/30004* (2013.01); *G06T 2207/30204* (2013.01)
USPC ........... 382/131; 382/128; 382/129; 382/130; 382/132; 600/431

(58) Field of Classification Search
USPC .................. 328/128–132; 600/431
See application file for complete search history.

(56) References Cited

U.S. PATENT DOCUMENTS 5,839,440 A * 11/1998 Liou et al. ...................... 600/431
2004/0052412 A1 * 3/2004 Wall et al. ..................... 382/159

(Continued)

FOREIGN PATENT DOCUMENTS

| WO | 2006082108 A2 | 8/2006 |
| WO | 2007100955 A2 | 9/2007 |
| WO | 2008062366 A2 | 5/2008 |

OTHER PUBLICATIONS

Brinks R. et al ("local compensation for respiratory motion in list-mode PET", Advanced in medical engineering, pp. 31-36, Springer, 2007).*

(Continued)

*Primary Examiner* — Amara Abdi

(57) ABSTRACT

A method includes generating a kinetic parameter value for a VOI in a functional image of a subject based on motion corrected projection data using an iterative algorithm, including determining a motion correction for projection data corresponding to the VOI based on the VOI, motion correcting the projection data corresponding to the VOI to generate the motion corrected projection data, and estimating the at least one kinetic parameter value based on the motion corrected projection data or image data generated with the motion corrected projection data. In another embodiment, a method includes registering functional image data indicative of tracer uptake in a scanned patient with image data from a different imaging modality, identifying a VOI in the image based on the registered images, generating at least one kinetic parameter for the VOI, and generating a feature vector including the at least one generated kinetic parameter and at least one biomarker.

30 Claims, 7 Drawing Sheets

(56) References Cited

U.S. PATENT DOCUMENTS

| | | | |
|---|---|---|---|
| 2008/0013814 A1* | 1/2008 | Carlsen | 382/131 |
| 2008/0037844 A1* | 2/2008 | Baumgart | 382/130 |
| 2008/0042067 A1* | 2/2008 | Rousso et al. | 250/363.04 |
| 2008/0167362 A1* | 7/2008 | Gao et al. | 514/406 |
| 2008/0230705 A1 | 9/2008 | Rousso et al. | |
| 2008/0267477 A1* | 10/2008 | Conti et al. | 382/131 |
| 2009/0232849 A1* | 9/2009 | Gallez et al. | 424/239.1 |
| 2009/0232916 A1* | 9/2009 | Shulman et al. | 424/752 |
| 2010/0082363 A1* | 4/2010 | Warner et al. | 705/2 |

OTHER PUBLICATIONS

M.E. Kamasak et al ("Direct reconstruction of Kinetic parameter images from dynamic PET data", IEEE transaction on medical imaging, vol. 24, No. 5, May 2005).*

Anderson, K. M., et al.; Cardiovascular disease risk profiles; 1991; Am Heart J.; 121:abstract.

Boellaard, R., et al.; The Netherlands protocol for standardization and quantification of FDG whole body PET studies in multi-centre trials; 2008; Eur. J. Nucl. Med. Mol. Imaging; 35:2320-2333.

Brinks, R., et al.; Local Compensation for Respiratory Motion in List-mode PET; 2007; Advances in Medical Engineering; pp. 31-36.

Castel, F., et al.; Quantitative techniques in 18FDG PET scanning in oncology; 2008; British Journal of Cancer; 98:1597-1601.

Gullberg, G. T., et al.; Estimation of the parameter covariance matrix for a one-compartment cardiac perfusion model estimated from a dynamic sequence reconstructed using map iterative reconstruction algorithms; 2008; Lawrence Berkeley National Laboratory; Paper LBNL-54155.

Janssen, M. H. M., et al.; Tumor Delineation Based on Time-Activity Curve Differences Assessed with Dynamic Fluorodeoxyglucose Positron Emission Tomography-Computed Comography in Rectal Cancer Patients; 2009; Int. J. Radiation Oncology Biol. Phys.; 73(2)456-465.

Kirov, A. S., et al.; Partial volume effect correction in PET using regularized iterative deconvolution with variance control based on local topology; 2008; Phys. Med. Biol.; 53:2577-2591.

Morita, K., et al.; Quantitative analysis of myocardial glucose utilization in patients with left ventricular dysfunction by means of 18F-FDG dynamic positron tomography and three-compartment analysis; 2005; Eur. J. Nucl. Med. Mol. Imaging; 32(7)806-812.

Naghavi, M., et al.; From Vulnerable Plaque to Vulnerable Patient a Call for New Definitions and Risk Assessment Strategies: Part I; 2003; Circulation, J. American Heart Assoc.; 108(15)1772-1778.

Nahrendorf, M., et al.; Nanoparticle PET-CT Imaging of Macrophages in Inflammatory Atherosclerosis; 2008; Circulation, J. American Heart Assoc.; 117:379-387.

Nishiyama; Y., et al.; Diagnostic value of kinetic analysis using dynamic FDG PET in immunocompetent patients with primary CNS lymphoma; 2006; Eur. J. Nucl. Med. Mol. Imaging; abstract.

Noterdaeme, O., et al.; Rigid and Non Rigid Registration for the Analysis of Contrast Enhanced Liver Magnetic Resonance Images; 2008; Proc. 12th Ann. Conf. on Medical Image Understanding and Analysis; pp. 256-260.

Rousset, O. G., et al.; Correction for Partial Volume Effects in PET: Principle and Validation; 1998; J. Nuclear Medicine; 39(5)904-911.

Rudd, J. H. F., et al.; Imaging Atherosclerotic Plaque Inflammation with 18F-Fluorodeoxyglucose Positron Emission Tomography; 2008; J. Nucl. Med.; 49(6)871-878.

Tohka, J., et al.; Deconvolution-based partial volume correction in Raclopride-PET and Monte Carlo comparison to MR-based method; 2008; Neuroimage; 39(4)1570-1584.

Zeng, G. L., et al.; Using Linear Time-Invariant System Theory to Estimate Kinetic Parameters Directly from Projection Measurements; 1995; IEEE Trans. on Nuclear Science; 42(6)2339-2346.

* cited by examiner

FUNCTIONAL IMAGING

CROSS REFERENCE TO RELATED APPLICATIONS

This application claims the benefit of U.S. provisional application Ser. No. 61/152,986 filed Feb. 17, 2009, which is incorporated herein by reference.

The following generally relates to functional imaging and finds particular application with positron emission tomography (PET); however, it also amenable to other medical and non-medical imaging applications.

Functional positron emission tomography (PET) imaging is used to image dynamic tracer uptake in tissue and provides quantitative information about the tissue. The development of tracers that target specific biological processes has enhanced the understanding of many diseases and processes. For example, there are a number of radiotracers that are used to target cellular proliferation and hypoxia or that are used in first-pass studies to study cardiac function. Many of these tracers are characterized by complex kinetics in which there is movement of tracer between different physical or chemically distinct states or compartments.

A semi-quantitative measure such as standard uptake value (SUV) is a commonly used metric for characterizing tumors in PET images. Kinetic analysis of tracer transport and retention provides quantitative measures of tracer uptake which might have a greater prognostic value. In the case of fluoro-deoxyglucose (FDG), kinetic analysis differentiates between tracer transport and dephosporylation (hexokinase activity) and retention, and takes into account variable plasma clearance rates. Unfortunately, SUV measures of FDG uptake are limited because they measure the total activity in the tumor, including both metabolized and un-metabolized FDG in the blood, in intracellular spaces, and in the cell.

In addition, accurate estimation of kinetic parameters, which is used in characterizing the underlying tracer distribution, is confounded by a number of factors including that of physiologic motion such as cardiac and respiratory motion. Methods to minimize blur due to motion include gating (cardiac, respiratory or both). However, the loss of counts with gating add to the challenge of fitting noisy time-activity curves in conventional PET or SPECT dynamic images.

Aspects of the present application address the above-referenced matters and others.

According to one aspect, a method includes generating at least one kinetic parameter value for a volume of interest (VOI) in a functional image of a subject based on motion corrected projection data using an iterative algorithm. The iterative algorithm includes determining a motion correction estimate for projection data corresponding to the VOI based on the VOI, motion correcting the projection data corresponding to the VOI to generate the motion corrected projection data, and estimating the at least one kinetic parameter value based on the motion corrected projection data or image data generated with the motion corrected projection data.

In another aspect, a method includes registering functional PET image data indicative of tracer uptake in a scanned patient with image data from a different imaging modality, identifying a volume of interest (VOI) in the image based on the registered images, generating at least one kinetic parameter for the VOI, and generating a feature vector that includes the at least one generated kinetic parameter and at least one bio-marker.

In another aspect, a method includes registering functional data indicative of tracer uptake in a scanned patient with image data from a different imaging modality, identifying a volume of interest (VOI) in the image based on the registered images, iteratively correcting the data for motion artifacts and generating at least one kinetic parameter for the VOI based on motion corrected data, and generating a feature vector that includes the at least one generated kinetic parameter and at least one bio-marker and/or clinical data.

In another aspect, a system includes a parameter determiner that generates at least one kinetic parameter value for a volume of interest (VOI) in functional image data of a subject based on motion corrected image data using an iterative algorithm. The parameter determiner includes a motion corrector that motion corrects functional image data, wherein the motion corrector corrects image data previously corrected for motion in a previous iteration of the iterative algorithm, and a parameter estimator that estimates at least one kinetic parameter value based on the motion corrected image data.

In another aspect, a system includes an image combiner that combines functional image data indicative of tracer uptake in a scanned patient with image data from a different imaging modality, a region of interest identifier that identifies a volume of interest (VOI) in an image based on the registered images, and a parameter estimator that generates at least one kinetic parameter for the VOI.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
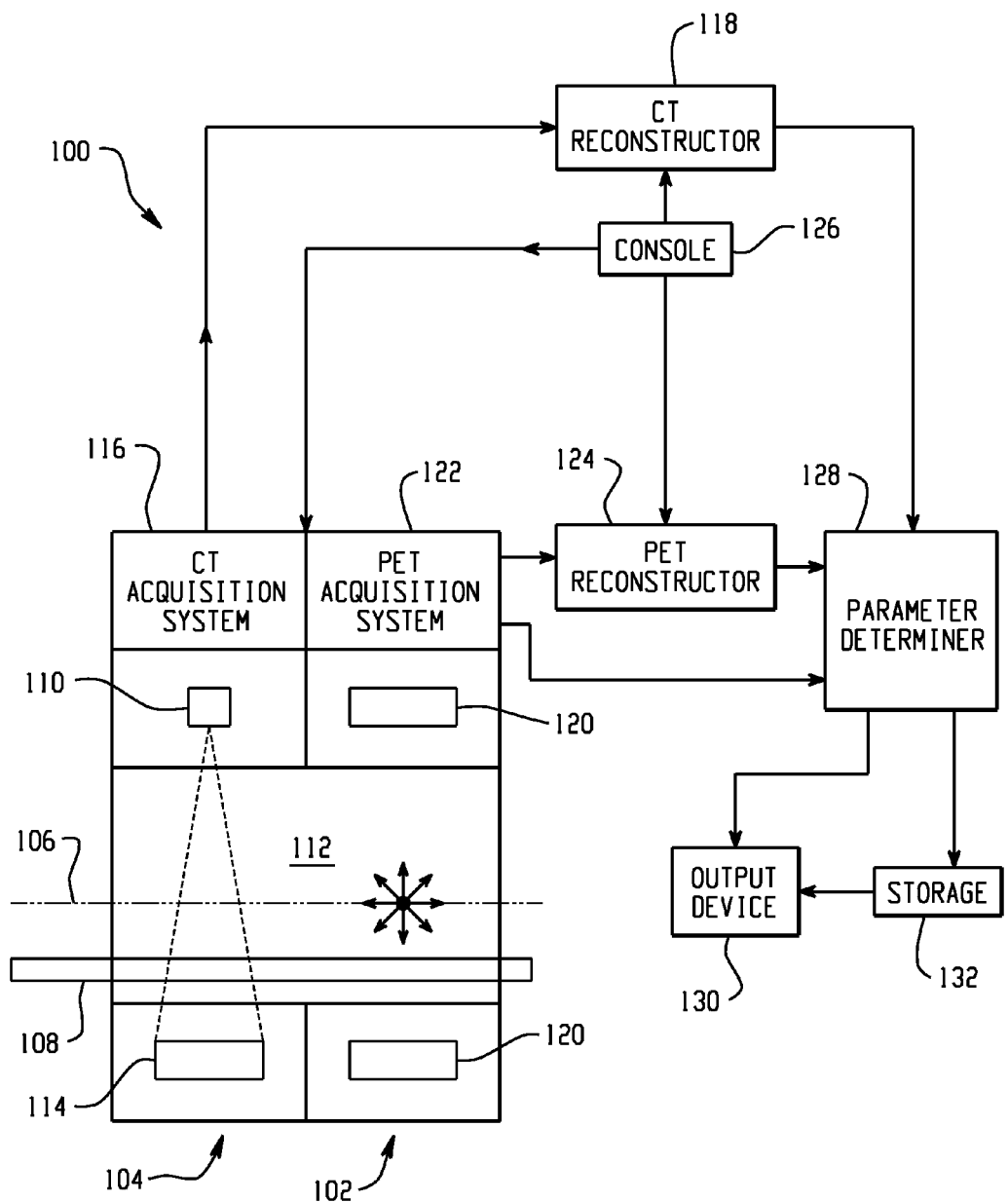
FIG. 1 illustrates an exemplary imaging system in connection with a kinetic parameter determiner.

FIG. 1 illustrates an imaging system 100, which includes a combined positron emission tomography/computed tomography (PET/CT) system with both a PET gantry portion 102 and a CT gantry portion 104. In another embodiment, the PET and CT portions respectively are part of separate CT and PET imaging systems, which can be located remote from each other, such as in different examination rooms. In still another embodiment, the CT gantry portion 104 is replaced with another imaging modality such as a magnetic resonance (MR) gantry portion. In yet another embodiment, the CT portion is omitted. In still another embodiment, the PET gantry portion 102 is replaced with another imaging modality such as a single photon emission computed tomography (SPECT) gantry portion.

The CT portion 104 includes a radiation source 110 such as an x-ray tube that rotates around an examination region 112 about the z-axis 106. An x-ray radiation sensitive detector array 114 detects radiation that traverses the examination region 112 and generates a signal indicative thereof. A CT acquisition system 116 processes the signal and generates CT projection data indicative of radiation attenuation along a plurality of lines or rays through the examination region 112. A CT reconstructor 118 reconstructs the CT projection data using a suitable reconstruction algorithm and generates image data indicative of the spatially varying radiation attenuation of the object or subject.

The PET gantry portion 102 includes a gamma ray radiation sensitive detector array 120 disposed about the examination region 112 in a generally ring-shaped or annular arrangement. A detector may include one or more scintillation crystals and corresponding photosensors, such as photomultiplier tubes, photodiodes, etc. A crystal produces light when struck by a gamma ray, and the light is received by one or more of the photosensors, which generates electrical signals indicative thereof. The detector array 120 detects gamma radiation characteristic of positron annihilation events occurring in the examination region 112 and generates a signal indicative thereof.

A PET data acquisition system 122 processes the signal and generates PET projection data such as a list of annihilation events detected by the detectors 120 during data acquisition. List mode projection data typically includes a list of the detected events, with each entry in the list including information such as a time at which the event was detected, as well as the position and orientation of the corresponding line-of-response (LOR). Where the system 100 is configured with time-of-flight (TOF) capabilities, an estimate of the position of the annihilation along the LOR is also provided. A PET reconstructor 124 reconstructs the PET projection data using a suitable reconstruction algorithm and generates image data indicative of the distribution of the radionuclide in the scanned object or subject.

The PET gantry portion 102 and the CT gantry portion 104 are disposed about a common longitudinal or z-axis 106. A support 108 supports an object or subject, such as a human or animal patient, to be imaged in an examination region 112. The support 108 is longitudinally movable in coordination with operation of the PET/CT system so that the object or subject can be scanned at a plurality of longitudinal locations by both the PET and CT gantry portions 102, 104.

An operator console 126 such as a computer includes a human readable output device such as a monitor or display and input devices such as a keyboard and mouse. A processor of the console 126 executes software or computer readable instructions encoded on computer readable medium, which allows the operator to perform functions such as selecting imaging protocols, initiating, pausing and terminating scans, viewing and/or manipulating the projection and/or image data, etc. The instructions, when executed, also perform various operations such as determine kinetic parameters, correct data for motion artifacts, generate feature vectors, determine risk metrics, etc.

A parameter determiner 128 determines at least one kinetic parameter based on the PET projection data, the PET image data, and/or the CT image data. As described in greater detail below, in one instance this includes determining the at least one kinetic parameter via an iterative approach that includes concurrent correction of PET projection data for motion artifacts. Also described in greater detail below, in another instance this includes determining the at least one kinetic parameter based on a combination of PET and CT image data, and generating a feature vector that includes the at least one kinetic parameter as well as one or more other bio-markers and/or clinical data. Such a vector can be analyzed to determine a health risk metric for the scanned patient.

The determined at least one kinetic parameter, the feature vector, the health risk metric and/or other information can be provided to an output device 130 such as a display or other information presenting device and/or to storage 132. The output device 130 and storage 132 are shown separate from the console 126 in this example and can be part of a workstation and/or other computing device. In another embodiment, at least one of the output device 130 or storage 132 are part of the console 126.

Figure 2:
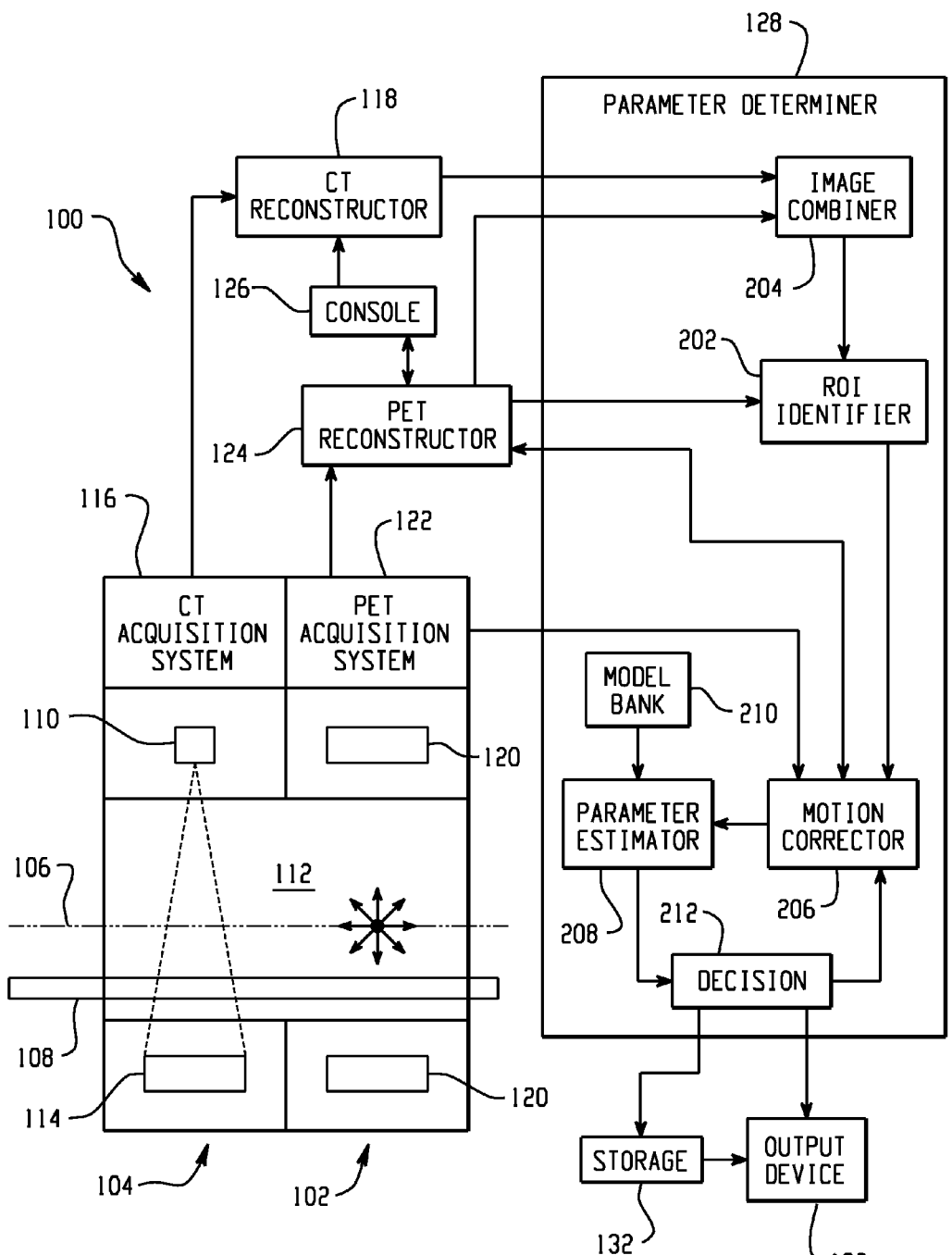
FIG. 2 illustrates an example kinetic parameter determiner that concurrently estimates kinetic parameters and corrects for motion artifact.

FIG. 2 shows an example embodiment in which the kinetic parameter determiner 128 is configured to determine the at least one kinetic parameter from the PET data via an iterative approach that includes concurrent correction of PET projection data for motion artifacts.

A region of interest (ROI) identifier 202 identifies a volume of interest (VOI) in the PET image data for kinetic analysis. The VOI may include an organ, a lesion, or other feature of interest of the object or subject.

In the illustrated example, the VOI is identified using CT image data. An image combiner 204 superimposes or fuses contrast or otherwise enhanced CT image data, which emphasizes a structure of interest such as a calcium deposit in a vessel, and corresponding PET image data using rigid and/or elastic registration techniques. The user and/or executing software can then identify the VOI in the PET image data in connection with the registered CT image data. The CT image data can be from the CT portion 104 or another CT system. As noted above, other imaging data such as MR image data can alternatively be used to facilitate identifying the VOI in the PET image data.

In another instance, the user manually identifies the VOI in the PET image data without other image data. In this instance, the CT portion 104 can be omitted from the system 100. In another instance, the VOI is identified using a priori information about the object or subject. In the case of a human patient, for example, the location of a VOI that includes an organ such as the heart or blood vessel may be estimated using known morphological characteristics and/or models.

A motion corrector 206 corrects the PET data for motion artifact based on the VOI. The corrected PET data can be reconstructed to generate motion corrected images. Motion of a subject may be measured using a suitable motion monitor such as a respiratory, cardiac, or other physiological monitor in the case of a human patient. Motion may also be detected via an analysis of the projection space and/or the image space data.

In one instance, the motion corrector 206 uses an estimate of motion for a center of mass of the VOI to shift the LORs passing through the VOI. A non-limiting example of suitable motion detection and compensation is described in Patent Application Ser. No. PCT/US2007/61597 filed on Feb. 5, 2007 and entitled "Local Motion Compensation Based on List Mode Data," which is incorporated herein by reference in its entirety.

A parameter estimator 208 estimates at least one kinetic parameter based on motion corrected data. In this example, the estimator 208 estimates the parameter based on motion corrected list mode projection data. In another embodiment, the motion corrected projection data is reconstructed via the PET reconstructor 124 or other reconstructor, and the estimator 208 estimates the kinetic parameter based on the reconstructed image data.

In the illustrated embodiment, the estimator 208 estimates the parameter based on a known compartmental model from a model bank 210. This may involve estimating tracer kinetics for the VOI using the known compartmental model. A suitable model includes a model that characterizes the dynamic behavior of the tracer, model parameters for kinetic analysis, and an estimate of the motion for the center of mass of the VOI.

A decision component 212 determines whether the at least one estimated kinetic parameter is within a predetermined range. For example, the decision component 212 may compare a present estimated value of a kinetic parameter with a previous estimated value of a kinetic parameter, or determine a difference between the present and previous values and compare the difference with a threshold.

In one instance, if the difference between values is within the predetermined range or less than a predetermined threshold value, then the estimated value of the kinetic parameter is presented via the output device 130, stored in the storage 132, and/or otherwise utilized.

If the difference between values is outside of the predetermined range or greater than the predetermined threshold value, then another motion correction and parameter estimation iteration can be performed in which the motion corrector 206 corrects the previously corrected PET data for motion artifact and the estimator 208 estimates the kinetic parameters based on the corrected data.

After each iteration or some predetermined number of iterations, the decision component 212 determines whether the latest estimated kinetic parameter is within the predetermined range. The decision component 212 may also terminate this iterative calculation after a predetermined number of iterations, a user input indicating termination, and/or otherwise.

The difference and/or threshold may be presented to the user via the output device 130, and a subsequent iteration may commence in response to user input and/or a computer automated approach.

The embodiment of FIG. 2 can be used to accurately estimate kinetic parameters that characterize underlying dynamics of tracers such as, but not limited to, Fluorodeoxyglucose (FDG), fluorothymidine (FLT), O-(2-[$^{18}$F]fluoroethyl)-L-tyrosine (FET), fluoromisonidazole (FMISO), and fluoroazomycinarabinofuranoside (FAZA), O15-H2O, etc. in the presence of motion using local motion compensation techniques.

Motion compensation can be performed in specific areas of interest, such as tumor lesions, while simultaneously estimating the kinetic parameters of the tracer distribution, providing quantitative parametric images, which can provide more specific biological measures. Since motion can be directly estimated from the list mode data, external gating sensors can be omitted. Furthermore, the loss of count statistics associated with respiratory or cardiac gating can be mitigated, which can lead to more accurate estimates of highly noise sensitive kinetic parameters for characterizing the tracer uptake.

Example applications include, but are not limited to, motion correction for PKM in cardiac perfusion imaging, where a moving organ and fast tracer kinetics (e.g., ammonia, rubidium, etc.) are combined. Another application is in the area of therapy response assessment, where accurate quantitative measures such as those provided by kinetic analysis can facilitate identifying patient responders from non-responders. For example, FDG or FLT flux estimates of lung nodule tumors that are corrected for respiratory motion could provide improved measures of response assessment.

Yet another application includes radiation therapy planning (RTP), where parametric images of FDG flux or FMISO k3 images, for example, corrected for motion artifacts could aid in the accurate delivery of radiation using IMRT techniques, providing maximum cell-kill, while minimizing morbidity to surrounding normal (risk) organs as parametric images based on kinetic analysis can provide relatively specific images related to the underlying biology of tumors such as proliferation, hypoxia, metabolism and/or other functional information with respect to semi-quantitative measures such as SUV, which can be affected by factors such as imaging time, variable plasma clearance rates, etc.

Figure 3:
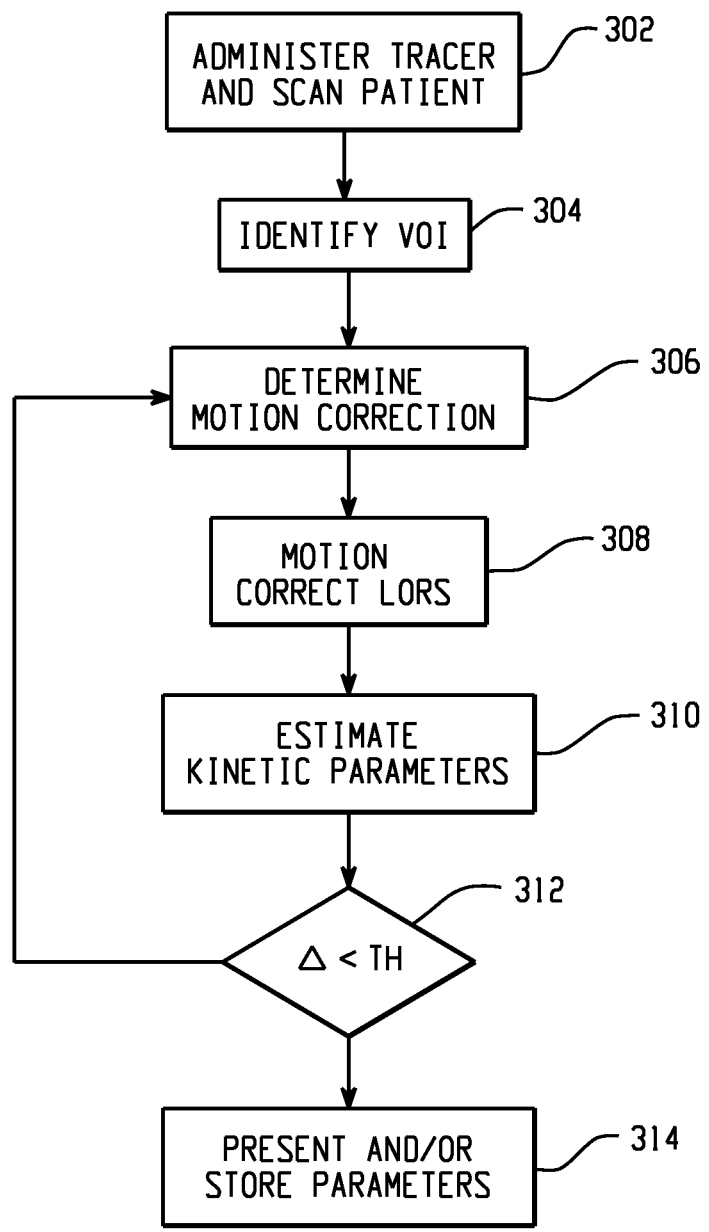
FIG. 3 illustrates a method employing the kinetic parameter determiner of FIG. 2.

FIG. 3 illustrates a method for determining at least one kinetic parameter via the system of FIG. 2.

At 302, a tracer such as FDG, FLT, FMISIO and/or other PET tracer is administered to a patient, and the patient is scanned.

At 304, a volume of interest (VOI) is identified in PET data. As discussed herein, this may include a manual or automated approach, with or without use of CT, MR, etc. data to facilitate identifying the VOI.

Figure 4:
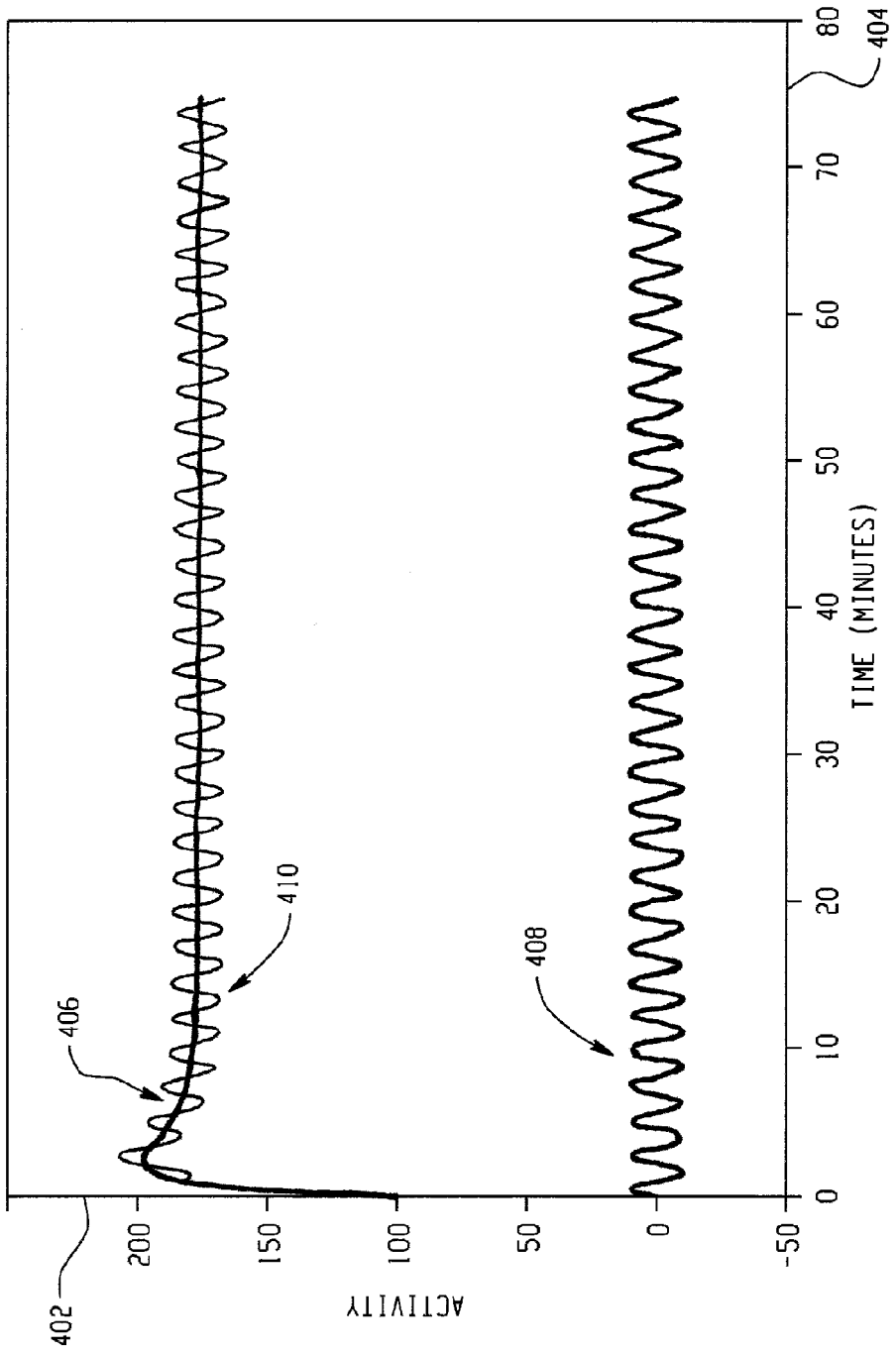
FIG. 4 illustrates a simulated time activity curve showing tracer uptake and motion induced modulation over time.

The data in the VOI may include motion artifact. By way of example, FIG. 4 illustrates a simulated FLT time activity curve (TAC). A first axis 402 represents activity and a second axis 404 represents time. A first curve 406 shows changes in tracer uptake over time (FLT TAC), and a second curve 408 shows motion induced modulation over time. A third curve 410 shows the measured TAC, which is a superposition of the tracer uptake and the motion induced modulation.

Returning to FIG. 3, at 306, a motion correction estimate is determined based on the VOI. This may include determining LOR x, y and/or z offsets and/or translations based on a center of mass of the VOI.

At 308, LORs traversing the VOI are motion corrected based on the determined motion correction. This may include shifting or otherwise correcting LORs based on the determined motion correction.

Figure 5A:
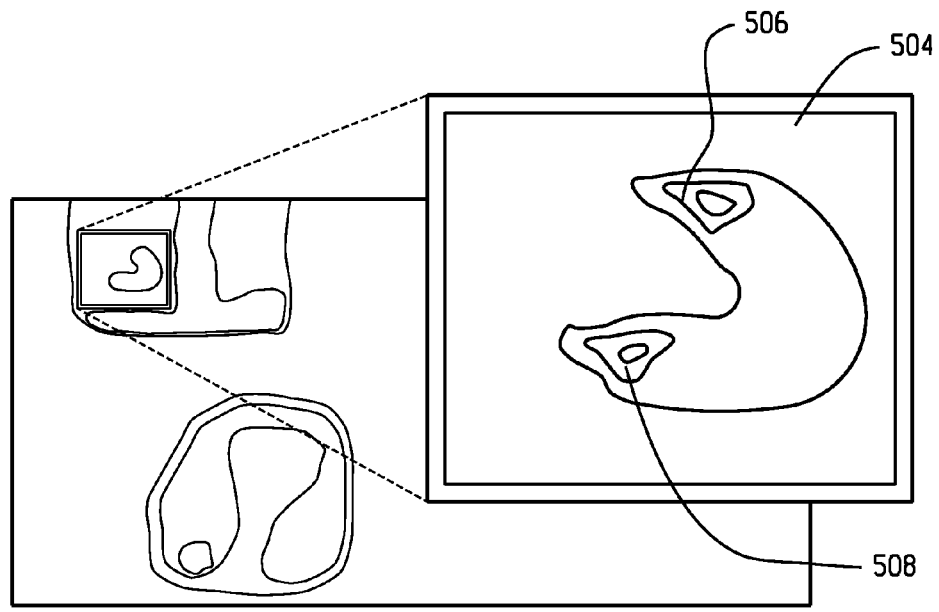
FIGS. 5A and 5B show images respectively generated with non-motion corrected data and motion corrected data.
Figure 5B:
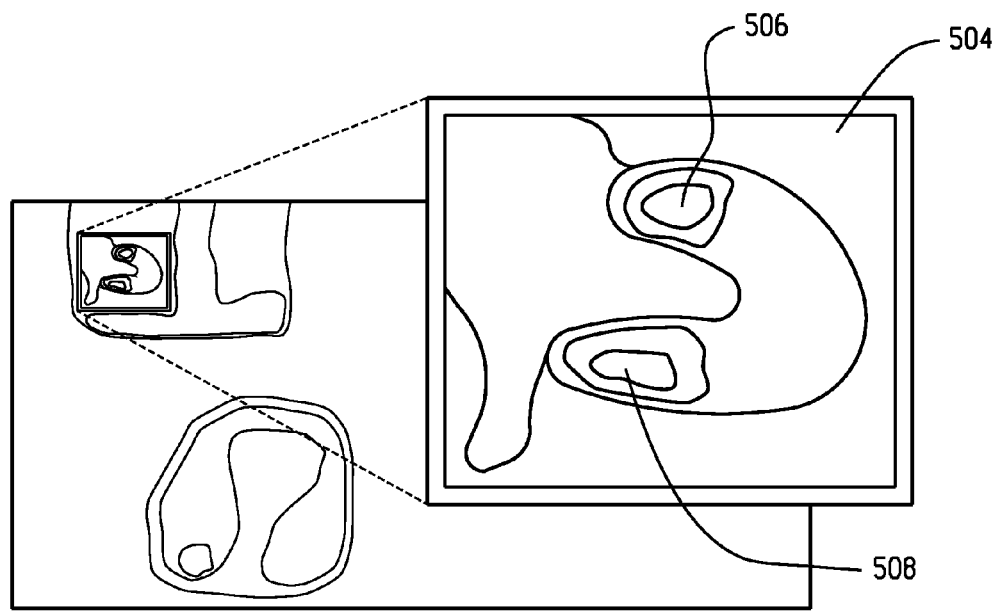

FIGS. 5A and 5B respectively show an image with respiratory induced motion modulation in a region of interest 504 and the image with motion corrected data in the region of interest 504. In this example, the motion correction resulted in an activity difference as shown at regions 506 and 508.

Returning to FIG. 3, at 310, model parameters are estimated based on the motion corrected projection data and/or image data generated from the motion corrected projection data. A suitable kinetic model (e.g., a compartmental and/or distributed model) and/or graphical methods such as Patlak or Logan plots can be pre-selected and used to characterize the time behavior of tracers.

By way of non-limiting example, a time-activity curve (TAC) for a dynamic PET acquisition can be modeled to include contributions from at least tracer uptake and motion, as shown below in Equation 1:

$$A_{measured}(t) = A_{tracer}(t) + A_{motion}(t); \qquad \text{EQUATION 1}$$

where $A_{measured}(t)$ represents the measured tracer concentration at time t, $A_{tracer}(t)$ represents the true tracer concentration at time t, and $A_{motion}(t)$ represents the underlying modulation of tracer concentration due to motion at time t. Other models may alternatively be used.

At 312, it is determined whether a difference ($\Delta$) between the presently estimated parameters and previous parameters is less than a predetermined threshold (TH). The previous parameters may be initial conditions or correspond to the previous estimation iteration.

If the difference ($\Delta$) is not less than the predetermined threshold, then acts 306 to 312 are repeated using the current (newly updated) motion corrected data, and if the difference ($\Delta$) is less than the predetermined threshold, then at 314 the resulting parameters are stored and/or presented.

The resulting parameters provide motion compensated kinetic model parameters and corresponding LOR offsets. As such, tracer kinetics can be estimated based on motion corrected data while concurrently correcting the data for motion.

Figure 6:
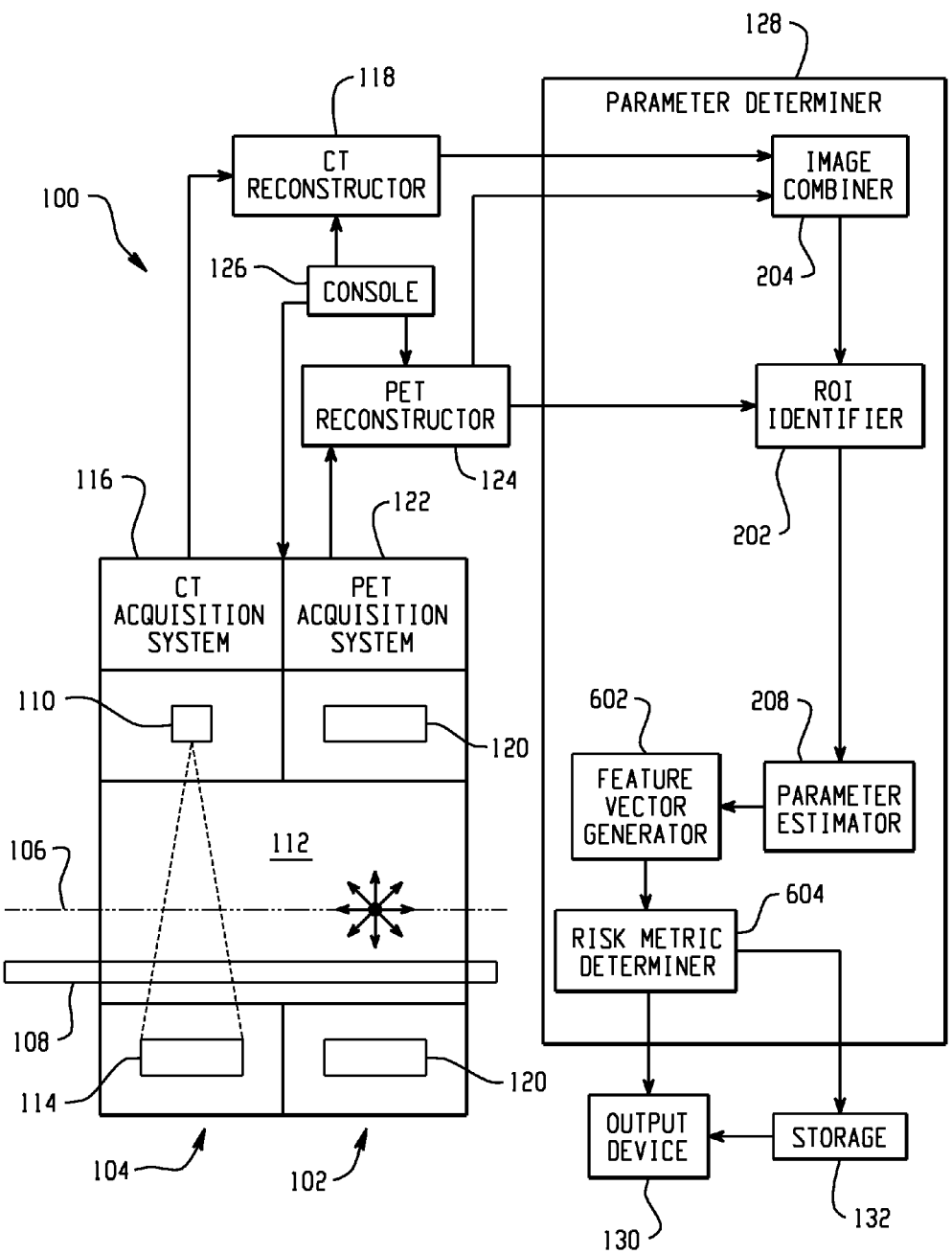
FIG. 6 illustrates an example kinetic parameter determiner that generates a feature vector that includes a kinetic parameter determined based on registered image data and at least one bio-marker and/or clinical data.

FIG. 6 shows an example embodiment in which the parameter determiner 128 determines at least one kinetic parameter using PET/CT imaging data. The system can alternatively or additionally take into account MR, SPECT, etc. data.

The image combiner 204 combines or otherwise fuses PET data and CT data corresponding to the same patient as described herein. The PET data may show FDG or other tracer uptake and the CT data may show contrast enhanced data. The image combiner 204 may use rigid and/or elastic registration techniques and/or other data combining techniques.

The ROI identifier 202 identifies a VOI in the PET data via the CT data. The VOI may include an organ, a lesion, or other feature of interest of the object or subject. The VOI may be identified through automated, manual or semi-automated techniques. Anatomical and/or other models may alternatively or additionally be used to identify the VOI in the PET data.

The parameter estimator 208 estimates at least one kinetic parameter based on the VOI. Parametric maps can be derived from pharmacokinetic modeling and provide an accurate and quantitative measure of FDG uptake and allow identification of areas of inflammation in the VOI.

A feature vector generator 602 generates a feature vector which includes the estimated kinetic parameter and at least one other bio-marker and/or clinical data. Examples of suitable bio-markers include, but are not limited to, a Framingham-score, glycosylated hemoglobin ($Hb_{A1c}$), high sensitivity C-reactive protein (hs-CRP), homocysteine, Tryptophan (Trp), etc. Suitable clinical data includes, but is not limited to, age, smoking habits, exercise levels, etc.

A risk metric determiner 604 determines a risk metric based at least on the feature vector. This may include determining a risk value for each feature and combining the risk values to determine the risk metric, variously weighting the risk values and summing them, or otherwise processing the data in the feature vector to determine a risk metric. The resulting risk metric may be stored in the storage 132, presented the output device 130 and/or otherwise utilized.

The embodiment of FIG. 6 can be used for various applications. For instance, it can be used to obtain a non-invasive measure of inflammation associated with high-risk plaque and can help refine risk due to atherosclerosis or other disease through a quantitative measure of vulnerable plaque inflammation, which can contribute to plaque destabilization that could result in clinically adverse events. Quantification of inflammatory activity allows for improved accuracy in diagnosis, therapy response monitoring, and assessment of disease development over time in longitudinal imaging procedures.

Figure 7:
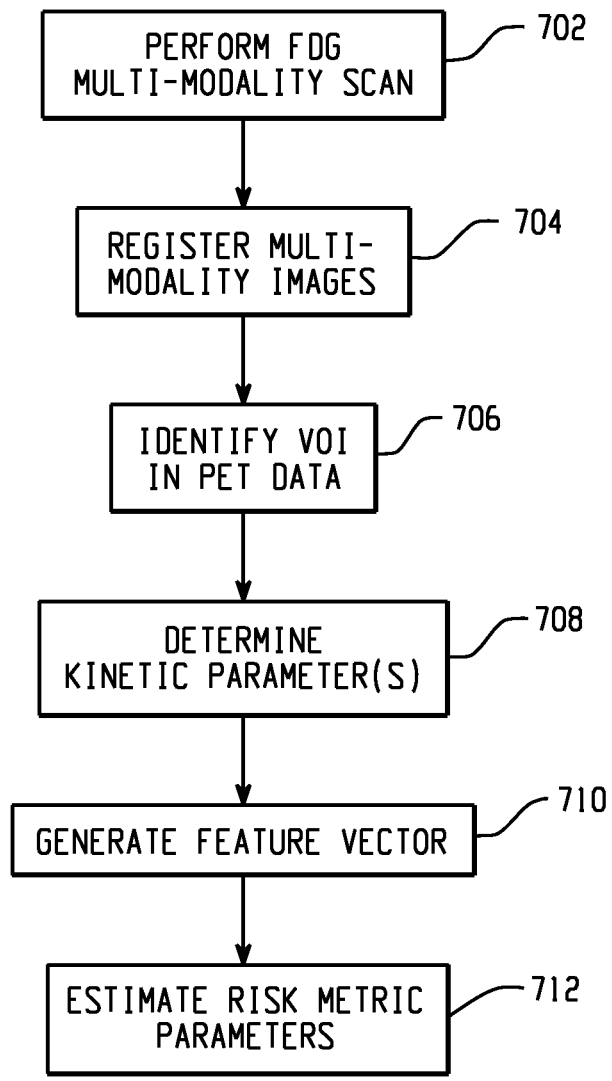
FIG. 7 illustrates a method employing the kinetic parameter determiner of FIG. 7.

FIG. 7 illustrates an example in which the system of FIG. 6 is used to provide a quantitative measure of vulnerable plaque inflammation using FDG PET/CT imaging.

At 702, inflammation imaging of vessels atherosclerosis, such as in connection with the carotid and/or peripheral artery, is performed with FDG PET/CT. Again, the CT scan can be substituted with an MR scan or the like.

At 704, the contrast-agent enhanced CT images are registered with the PET images.

At 706, one or more VOIs are identified and/or segmented using the registered images.

The FDG PET data can be corrected for partial volume effects using CT based priors (e.g., using segmented CT volumes of the carotids), de-convolution techniques using measured system response functions, and/or otherwise.

At 708, at least one kinetic parameter is determined based on the VOI. The kinetic analysis may include using parametric maps derived from pharmacokinetic modeling to determine a quantitative measure of FDG uptake and identify areas of inflammation.

At 710, a feature vector is generated and includes the uptake measures of inflammation (e.g., FDG Flux=$k1k3/(k2+k3)$, SUV, tissue to blood, etc) and at least one bio-marker for the patient.

At 712, a risk metric is generated based on the feature vector and is analyzed relative to a predetermined threshold value or range, or evaluated using an automatic decision support algorithm to determine a risk metric that can be used to determine if the patient has a risk for sudden cardiac event due to atherosclerosis.

The risk metric can provide a quantitative measure of vulnerable plaque inflammation and can be used to identify vulnerable patients for atherosclerotic disease. As noted above, quantification of inflammatory activity may allow for analysis that can lead to improved accuracy in diagnosis, therapy response monitoring, assessment of disease development over time in longitudinal imaging procedures, etc.

Those of ordinary skill in the art will recognize that the various techniques described above may be implemented by way of computer readable instructions stored on a computer readable storage medium accessible to a computer processor. When executed, the instructions cause the processor(s) to carry out the described techniques. Note that the medium need not be local to the processor; the instructions may be downloaded or otherwise accessed via a communication network such as the internet. The relevant computers may also be located remote from the imaging system, with the scan data transferred via a suitable network or other medium. The described techniques need not be performed concurrently with the data acquisition.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

The invention is claimed to be:

1. A method, comprising:
   (a) determining a motion correction estimate for projection data corresponding to a volume of interest (VOI) in a functional image of a subject based on the VOI;
   (b) motion correcting the projection data corresponding to the VOI with the motion corrected estimate to generate current motion corrected projection data;
   (c) estimating at least one kinetic parameter value based on the current motion corrected projection data, wherein the at least one kinetic parameter value; is a current kinetic parameter value:
   (e) determining a next motion correction estimate for the current corrected projection data corresponding to the VOI based on the VOI;
   (f) motion correcting the current corrected projection data corresponding to the VOI with the next motion corrected estimated to update the current motion corrected projection data;
   (g) setting the current motion corrected projection data equal to the updated current motion corrected projection data; and
   (h) estimating a next kinetic parameter value based on the current motion corrected projection data.

2. The method of claim 1, further including determining a difference between a value of the estimated current kinetic parameter value and a value of a previous kinetic parameter, wherein (e)-(h) are performed only if the difference is greater than a predetermined threshold value.

3. The method of claim 1, wherein determining the motion correction includes determining x, y and z offsets for at least one line-of-response traversing the VOI.

4. The method of claim 3, wherein motion correcting the projection data includes shifting the at least one line-of response based on the x, y and z offsets.

5. The method of claim 1, wherein estimating the at least one kinetic parameter value includes employing a model that includes a first contribution representing tracer uptake and a second contribution representing motion.

6. The method of claim 1, further comprising:
registering image data with image data from a different imaging modality, and
identifying the VOI in the image data based on the registered image data.

7. The method of claim 1, further comprising:
reconstructing projection data, including the motion corrected projection data corresponding to the VOI; and
generating a motion corrected image based on the reconstructed projection data.

8. The method of claim 1, wherein (e)-(h) are repeated until a predetermined number of iterations are performed.

9. The method of claim 1, wherein (e)-(h) are repeated in response to an input from a user.

10. The method of claim 1, further comprising:
concurrently correcting for motion artifacts and estimating kinetic parameter values for each iteration.

11. The method of claim 1, further comprising:
registering the functional image with image data from a different imaging modality;
identifying a volume of interest (VOI) in an image based on the registered images; and
generating the next kinetic parameter for the VOI.

12. The method of claim 11, further comprising generating a feature vector that includes the next kinetic parameter and at least one bio-marker.

13. A method, comprising:
registering functional image data indicative of tracer uptake in a scanned patient with image data from a different imaging modality;
identifying a volume of interest (VOI) in an image based on the registered images;
motion correcting projection data corresponding to the VOI to generate first motion corrected projection data;
generating at least one kinetic parameter for the VOI based on the first motion corrected projection data;
determining a motion correction estimate for the first motion corrected projection data corresponding to the VOI based on the VOI;
motion correcting the first motion corrected projection data corresponding to the VOI to generate second motion corrected projection data;
estimating at least a second kinetic parameter value based on the second motion corrected projection data; and
generating a feature vector that includes the at least second generated kinetic parameter and at least one bio-marker.

14. The method of claim 13, further comprising: determining a health risk metric based on the generated feature vector.

15. The method of claim 13, further comprising: determining at least one of pre or post treatment efficacy based on the health risk metric.

16. The method of claim 13, wherein the at least second kinetic parameter is generated based on a parametric map derived from pharmacokinetic modeling.

17. The method of claim 13, wherein the at least second kinetic parameter is indicative of one of a tracer uptake measures of inflammation.

18. The method of claim 13, wherein the at least second kinetic parameter is indicative of plaque inflammation in the circulatory system of the patient.

19. The method of claim 13, wherein the at least one bio-marker information indicative of one or more of glycosylated hemoglobin ($Hb_{A1c}$), high sensitivity C-reactive protein (hs-CRP), homocysteine, and Tryptophan (Trp).

20. The method of claim 13, wherein the image data from a different imaging modality is computed tomography image date.

21. A system, comprising:
a parameter determiner that generates at least one kinetic parameter value for a volume of interest (VOI) in functional image data of a subject based on motion corrected projection data using an iterative algorithm, the parameter determiner includes:
a motion corrector that motion corrects functional projection data, wherein the motion corrector corrects projection data previously corrected for motion in a previous iteration of the iterative algorithm, generating next different motion corrected projection data; and
a parameter estimator that estimates at least one kinetic parameter value based on the next different motion corrected projection data.

22. The system of claim 21, further including:
a decision component that validates the estimated at least one kinetic parameter value based on a previously estimated kinetic parameter, wherein the motion corrector corrects the previously corrected projection data in a subsequent iteration when a difference between the estimated at least one kinetic parameter value and the previously estimated kinetic parameter is greater than a predetermined threshold.

23. The system of claim 21, wherein the motion corrector determines a motion correction that includes x, y and z offsets for at least one line-of-response traversing the VOI.

24. The system of claim 23, wherein the motion corrector corrects the image data by shifting the at least one line-of response based on the x, y and z offsets.

25. The system of claim 21, further comprising a model bank that includes a model for estimating the at least one kinetic parameter value based on tracer uptake and motion.

26. The system of claim 21, further comprising:
a feature vector generator that generates a feature vector that includes the at least one generated kinetic parameter and at least one bio-marker.

27. The system of claim 26, further comprising:
a risk metric determiner that determines a health risk metric based on the generated feature vector.

28. The system of claim 26, wherein at least one of the feature vector or the risk metric is used to determine at least one of pre or post treatment efficacy.

29. The system of claim 21, wherein the at least one kinetic parameter is generated based on a parametric map derived from pharmacokinetic modeling.

30. The system of claim 21, wherein the at least one kinetic parameter is indicative of inflammation.

* * * * *